(12) United States Patent
Schlenoff et al.

(10) Patent No.: US 8,155,724 B1
(45) Date of Patent: Apr. 10, 2012

(54) BRAIN IMPLANTABLE ELECTRODES HAVING AN INCREASED SIGNAL TO NOISE RATIO AND METHOD FOR MAKING SAME

(75) Inventors: Joseph Schlenoff, Tallahassee, FL (US); Gilbert Case, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 18 days.

(21) Appl. No.: 12/834,094

(22) Filed: Jul. 12, 2010

Related U.S. Application Data (62) Division of application No. 11/622,553, filed on Jan. 12, 2007, now Pat. No. 7,754,063.

(60) Provisional application No. 60/758,420, filed on Jan. 12, 2006.

(51) Int. Cl.
| | |
|---|---|
| *A61B 5/04* | (2006.01) |
| *A61B 5/0408* | (2006.01) |
| *A61B 5/042* | (2006.01) |
| *A61B 5/05* | (2006.01) |
| *A61B 5/053* | (2006.01) |

(52) U.S. Cl. ........ 600/372; 600/373; 600/374; 600/377; 600/378; 600/395; 204/403.01; 435/287.1

(58) Field of Classification Search .................. 600/372, 600/373, 374, 377, 378, 395; 204/403.01; 435/287.1
See application file for complete search history.

(56) References Cited

U.S. PATENT DOCUMENTS

| 5,034,192 | A | * | 7/1991 | Wrighton et al. | .......... 422/82.02 |
| 2005/0106708 | A1 | * | 5/2005 | Xing et al. | .................. 435/287.1 |
| 2005/0148043 | A1 | * | 7/2005 | Dale | .............................. 435/26 |

* cited by examiner

*Primary Examiner* — Bruce Bell
(74) *Attorney, Agent, or Firm* — Allen, Dyer, Doppelt, Milbrath & Gilchrist, P.A.

(57) ABSTRACT

Herein disclosed are an electrode and a method for making an electrode having an enhanced electrically effective surface providing an increased signal to noise ratio. The electrode having a metal surface selected from gold, tungsten, stainless steel, platinum, platinum-tungsten, platinum-iridium, and combinations thereof; and an electrically conductive coating on said metal surface, said coating consisting essentially of polymerized pyrrole.

9 Claims, 8 Drawing Sheets

BRAIN IMPLANTABLE ELECTRODES HAVING AN INCREASED SIGNAL TO NOISE RATIO AND METHOD FOR MAKING SAME

RELATED APPLICATION

This application is a division of U.S. application Ser. No. 11/622,553 which was filed on Jan. 12, 2007, and which is now U.S. Pat. No. 7,754,063 issued on 13 Jul. 2010, and which claimed priority from U.S. provisional application Ser. No. 60/758,420 filed on Jan. 12, 2006.

FIELD OF THE INVENTION

The present invention relates to the field of microelectrodes and, more particularly, to microelectrodes especially configured for obtaining electrical signals from the brain.

BACKGROUND OF THE INVENTION

Researchers have, for many years, employed electrodes implanted directly into the brains of experimental animals for obtaining electrical data from brain tissue. Challenges in this endeavor have been the types of metals that are amenable for such use without causing adverse biological reactions and the size of theses electrodes, as well as limitations in their available surface area for collecting the weak electrical signals produced in the brain. Therefore, increasing the signal to noise ratio for brain-implantable electrodes has been one parameter needing improvement.

SUMMARY OF THE INVENTION

With the foregoing in mind, the present invention advantageously provides brain-implantable electrodes coated with a layer of an electrically conductive polymer and a method for making such electrodes.

In a preferred embodiment of the present invention, an electrode having an enhanced electrically effective surface providing an increased signal to noise ratio comprises a metal surface selected from gold, tungsten, stainless steel, platinum, platinum-tungsten, platinum-iridium, and combinations thereof, and an electrically conductive coating on said metal surface, said coating consisting essentially of polymerized pyrrole. In this electrode, the polymerized pyrrole coating provides a plurality of surface microcavities. That is, the electrically conductive coating forms a new surface on said electrode, said new surface disposed with a plurality of microcavities which increase total electrically effective surface on said electrode, thereby causing said electrode to have an increased signal to noise ratio. The electrically conductive coating has a surface disposed with a plurality of microcavities of up to 500 nm in depth and separation.

The present invention also includes a method of increasing the electrically effective surface area of an electrode. The method comprises connecting a metal electrode to a positive terminal in an electrolytic chamber having negative terminal and a power supply capable of delivering a constant amperage. The method continues by adding to the chamber a volume of an electrolytic bath so that the electrode is submerged therein, the electrolytic bath consisting essentially of distilled water, a soluble concentration of pyrrole, 98%, a soluble concentration of p-toluene-sulfonate, 95%, and mercapto-ethane-sulfonic acid in approximately one tenth the concentration of pyrrole and p-toluene-sulfonate. Finally, the method calls for coating the electrode with an electrically conductive layer of polymerized pyrrole by energizing the power supply to pass through the electrolytic bath a current of approximately 1 µAmp for a time sufficient to effect deposition of polymerized pyrrole on the electrode. In the method, it is preferred that the metal electrode contain one or more metals selected from gold, tungsten, stainless steel, platinum, platinum-tungsten, platinum-iridium, and combinations thereof. In practicing the method, deposition may be monitored and/or verified by measuring to determine that the depositing step causes a decrease in electrode impedance. The decrease in electrode impedance should be proportional to the amount of coating deposited. Additionally, depositing provides the electrode with a plurality of microcavities formed in the deposited electrically conductive layer.

In the method of coating, the chamber contains an electrolytic solution consisting essentially of a volume of distilled water, a soluble concentration of pyrrole, 98%, a soluble concentration of p-toluene-sulfonate, 95%, and mercapto-ethane-sulfonic acid in approximately one tenth the concentration of pyrrole and p-toluene-sulfonate. More specifically, in the electrolytic solution the volume of distilled water is approximately 50 ml, the soluble molar concentration of 98% pyrrole is approximately 0.1 M, the soluble molar concentration of 95% p-toluene-sulfonate is approximately 0.1 M, and the mercapto-ethane-sulfonic acid molar concentration is approximately 0.01 M.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1:
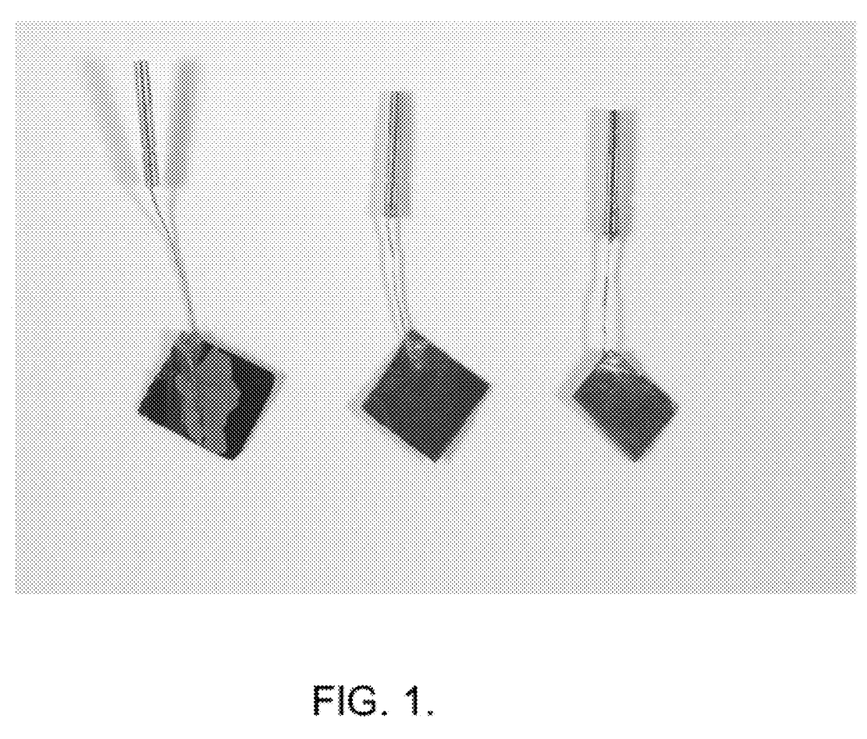
FIG. 1 displays macroelectrodes showing conductive polymer coatings of polypyrrole and polyaniline: on the left, polypyrrole; center, polyaniline with a higher deposition current; right, polyaniline with a lower deposition current; all according to an embodiment of the present invention.

FIGS. 1-8 illustrate various aspects of the present invention. In that regard, FIG. 1 depicts the first success of coating our macro-electrodes with a special conductive polymer was obtained after we tested various conductive polymer coatings under different protocols using macro-electrodes as shown. The macro-testing procedure was helpful in quickly testing the adhesion, consistency and porous layering of the polymer coating.

We utilized the SEM and Atomic Force Microscope to physically observe and measure the three dimensional nature of the coating. We also determined the basic electrolytic bath and electronic setup to control the deposition process. We set up the ongoing deposition process and animal testing and found a specific deposition protocol to give us the porosity we required. We found that we could deposit our conductive polymers on different metals, such as: gold, tungsten, stainless steel, platinum, platinum-tungsten and platinum-iridium. These are the metals that have been found through experience that the brain finds friendly and without toxic reactions. For instance, typically, it is known that aluminum and silver are not suitable for use in brain implants remaining in the brain longer than approximately 2 days, due to toxic reactions.

Figure 2:
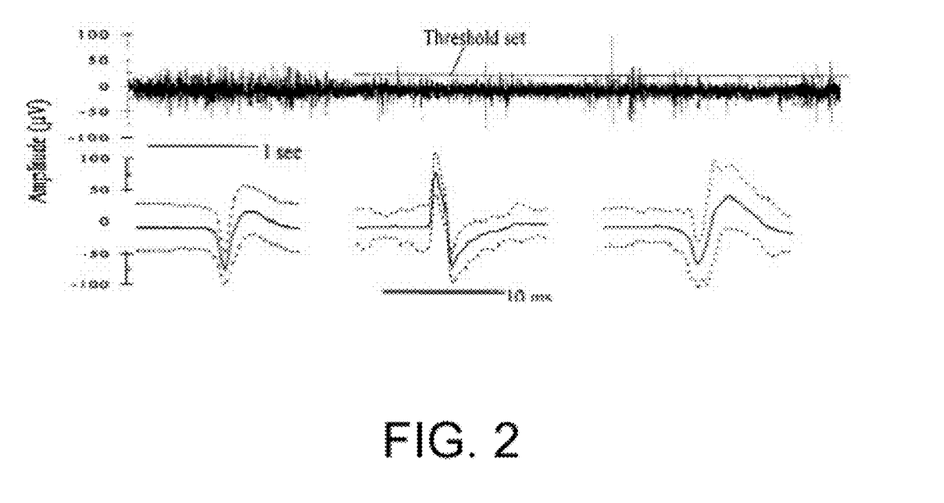
FIG. 2 depicts single-unit recordings and isolated neural action potentials and shows an actual recording of data taken using our conductive polymer coating with microelectrodes in an anesthetized hamster.

For neural recordings, data acquisition was accomplished with the Tucker-Davis system, which allowed us to graphically record all neural signals for our experiments. For example, the upper portion of FIG. 2 shows actual data of one of our olfactory single-unit microelectrode recordings, which captures three separate neural signals (lower portion of FIG. 2) on a single recording channel. These microelectrodes were coated with our conductive polymer. We can correlate these neural activities with a sensory cue of a specific odor and can determine exactly which neuron is odor sensitive and its pattern of activity related to the odor. FIG. 2 shows an actual recording of data taken using our conductive polymer coating with microelectrodes in an anesthetized hamster. The data obtained exhibited an estimated 2:1 increase in the signal-to-noise ratio as compared to signal strengths obtained in over 20 previous experiments using uncoated electrodes.

Figure 3:
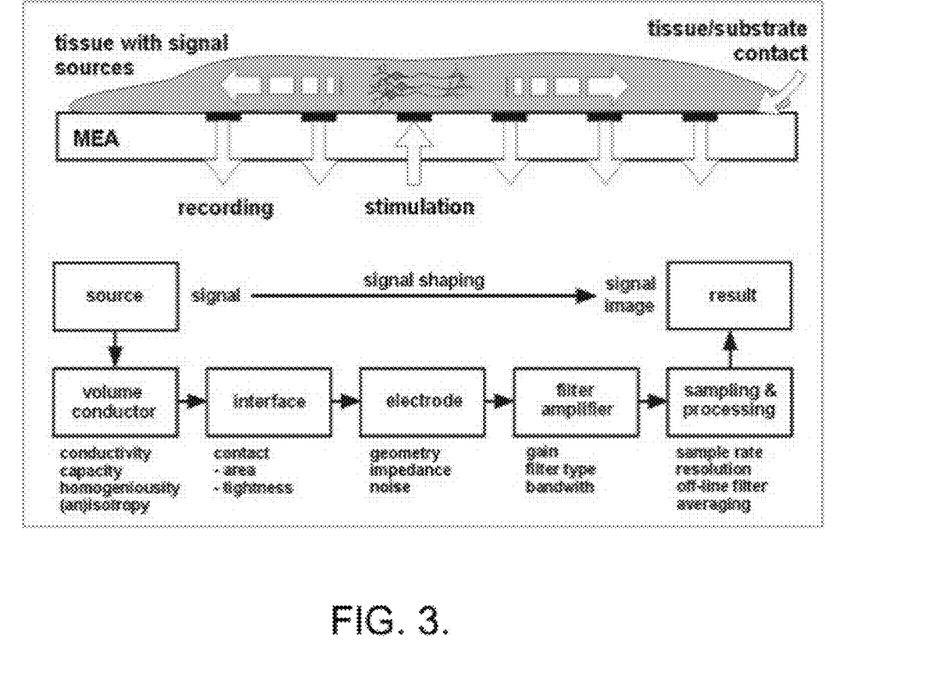
FIG. 3 is a flow diagram of the process and technical parameters in obtaining viable multiple electrode array (MEA) experimental results (Source: Multi-Channel Systems website, a partner to Product Licensee#2, ALA Scientific Instruments)

The technical parameters shown in FIG. 3 were used when recording from a Multiple Electrode Array (MEA). These technical considerations are quite similar to those required to obtain good single and multiple unit data in an awake animal. In order to get proper recordings, as those shown in FIG. 2, the signal shaping is mainly controlled by the electrode geometry, impedance and noise. Our conductive polymer coating allows the researcher to achieve more control over the impedance and drive the noise down, which results in a higher signal-to-noise ratio. This delivers a significantly improved signal, thereby enabling the researcher to complete the sensory analyses, as opposed to not being able to distinguish the noise from the signal. These principles apply to recordings from any brain area and to over 200 types of insertion electrodes. Such an improvement of signal-to-noise ratio as disclosed in the present invention enables smaller signals to be revealed and recorded, thereby allowing a better understanding of brain function in the recorded area.

Figure 4:
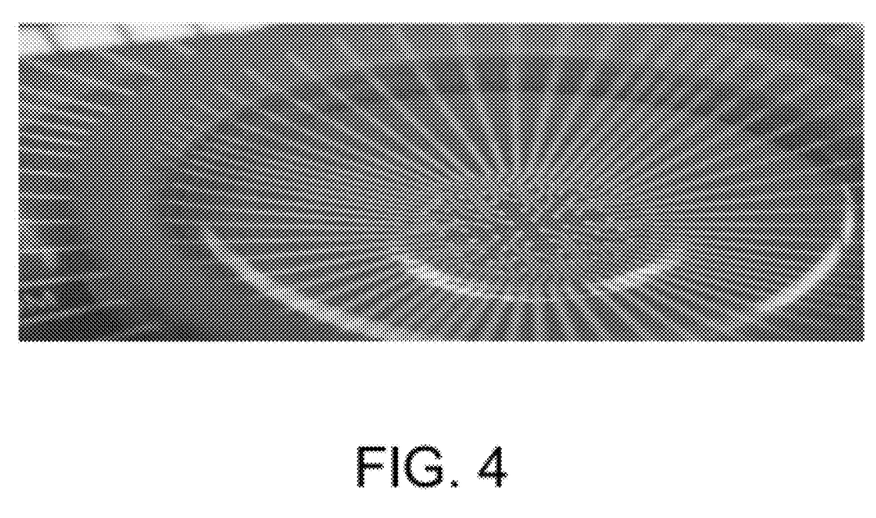
FIG. 4 shows an MEA for "in-vitro" type brain slice experiments.
Figure 5:
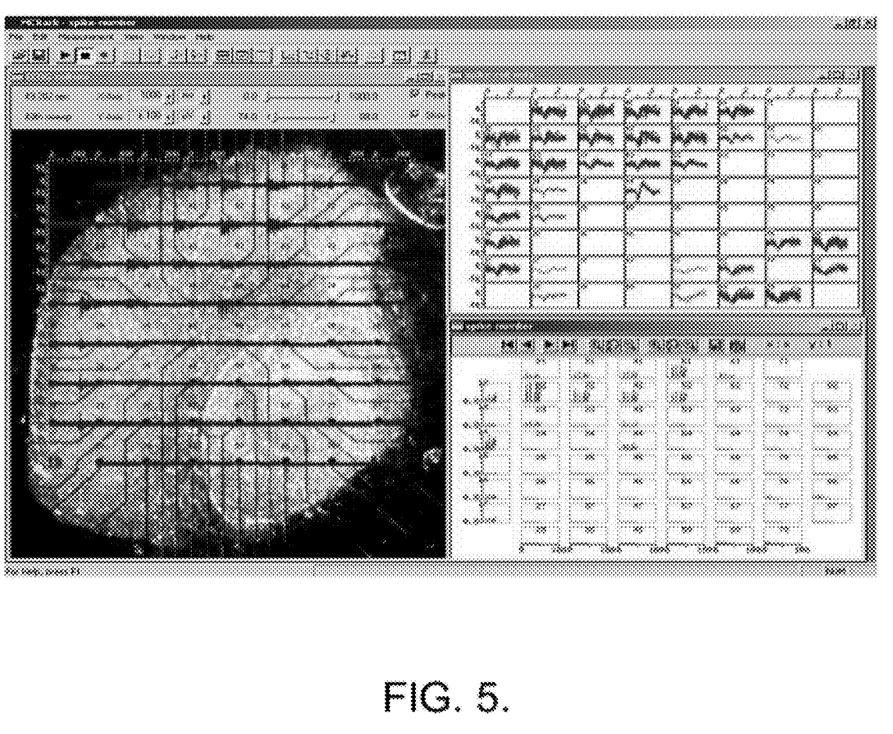
FIG. 5 illustrates an MEA with live tissue and an overlay of neural signals from the tissue.
Figure 6:
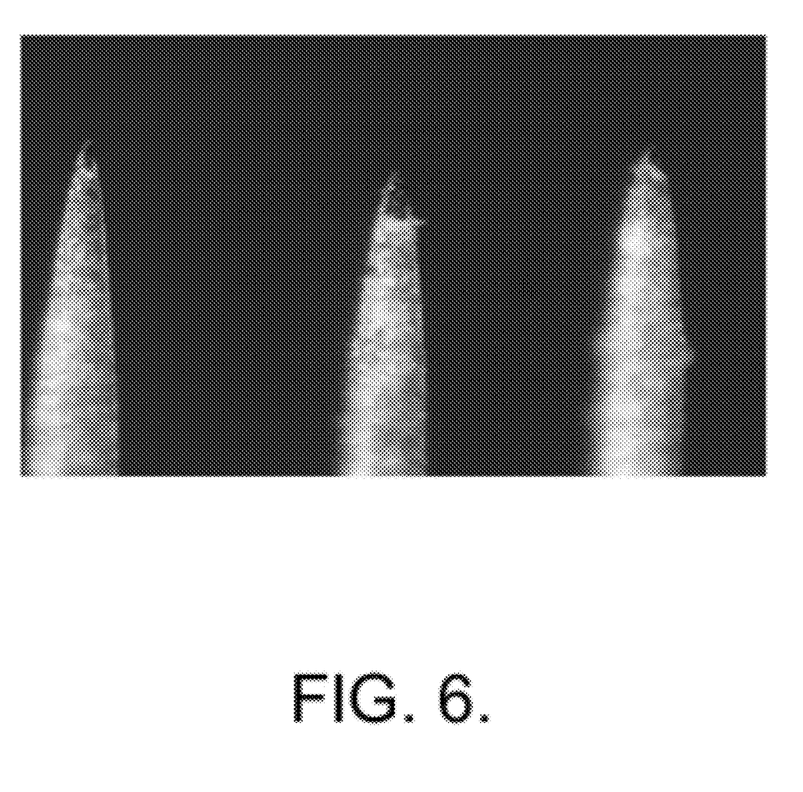
FIG. 6 is a photograph of the exposed metal tips of an insertion microelectrode array; three of eight tips are shown; spacing between electrodes is approximately 400 micrometers; length of this array is approximately 30 millimeters.

FIG. 4 shows an actual MEA device without any incubated brain slices. FIG. 5 shows an incubated brain slice and neural recordings from that incubated tissue. FIG. 6 shows a sample (only one of hundreds) of insertion electrodes. Over 95% of researchers who obtain neural recordings from animals and humans do so by using some form of insertion microelectrodes. These insertion electrodes range in diameter from 40 microns to 500 microns and in length from 2 millimeters to over 80 millimeters. Some deep brain studies in human require electrodes over 8 inches in length.

Process for Coating Microelectrodes with the Conductive Polymer.

A. The process begins with an electrolytic bath. We prepared the chemical solution for the electrolytic bath as follows:
1. Add 50 ml of distilled water to a clean electrolytic chamber. The circular negative electrolytic plate was made of heavy gauge platinum wire.
2. Add 0.1M of Pyrrole, 98%.
3. Heat 50 degrees C. and stir into solution for 5 minutes.
4. Add 0.1M of Sodium p-toluene-sulfonate, 95%.
5. Continue heating and stir for another 5 minutes.
6. Add 0.01M of MES (mercapto-ethane-sulfonic acid).
7. Continue heating and stir for another 5 minutes.

B. Once a fresh batch of the electrolytic solution is prepared, hook up the insertion-type microelectrodes to the positive connection of the constant amperage isolation unit. The plating protocol is as follows.
1. Insert the metal tips of the microelectrodes into the electrolytic bath making certain that the microelectrodes are positioned in the center area of the curved negative plate. This will promote formation of an even coating of conductive polymer on the microelectrode tips.
2. Record the impedance of each microelectrode before starting the deposition process. These values will typically vary between 1 MegOhm and 10 MegOhms.
3. Pump in 1 microAmp of current through the microelectrodes for 5 minutes via the isolation unit.
4. Verify and record the impedance measurement of each microelectrode after the deposition process is complete. One should observe a marked decrease in impedances. Normally a 3 MegOhm impedance will drop to 500-800K Ohms after deposition.
5. Further verification is done by observing the black coating on the micro tips of the electrodes.

Figure 7:
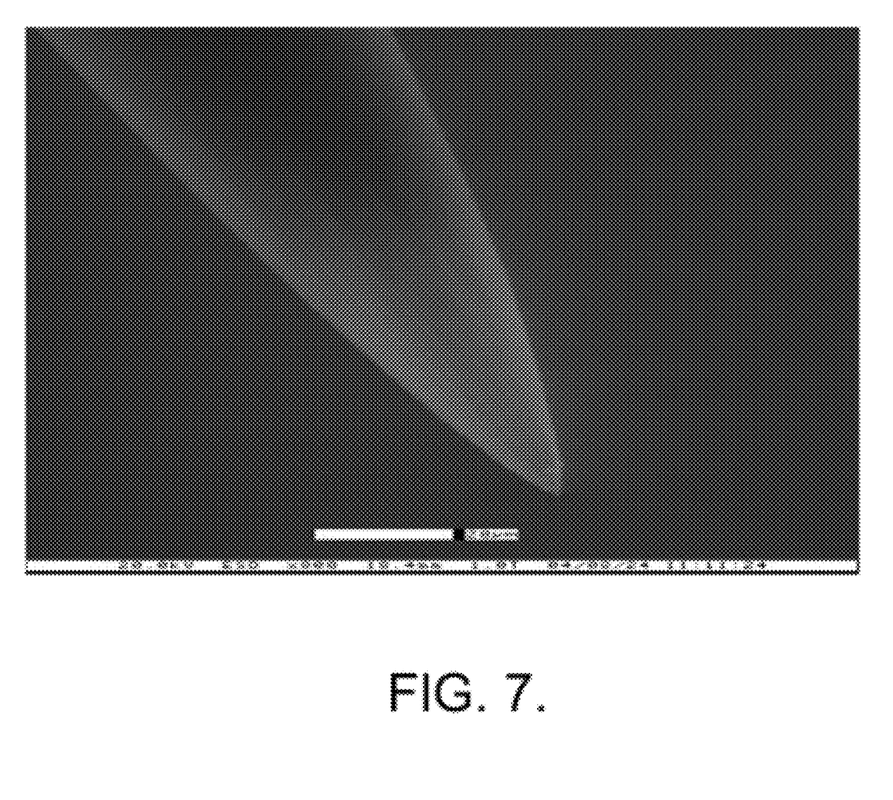
FIG. 7 is a scanning electron microscope (SEM) photograph of the tip of an insertion microelectrode, shank diameter of approximately 40 microns.
Figure 8:
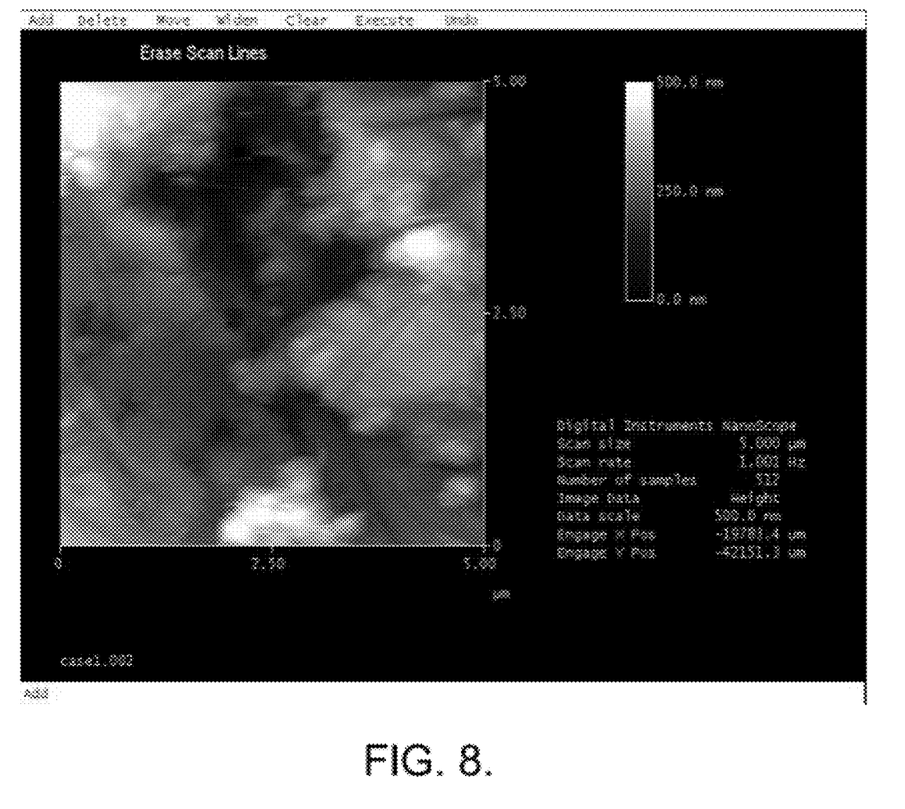
FIG. 8 is an atomic force microscope (AFM) photograph of the deposition of our conductive polymer coating on a flat macro-electrode.

C. During the original experiments to develop this process, we used the both the Scanning Electron Microscope (SEM) and the Atomic Force Microscope (AFM) to measure the micro-porosity of the conductive polymer coating. FIG. 7 shows an SEM photo (800×) of the tip of one insertion microelectrode. The ultra white area at the point is the exposed metal surface of less than 5 microns; that is the area coated with our conductive polymer. The microelectrode shown FIG. 8 shows an AFM photo of that process. One can clearly see micro-cavities ranging from 0 nano-meters to 500 nano-meters in depth and separation.

D. After the electrodes are coated with the conductive polymer, we store them in a foam holder within an enclosed plastic case. After six weeks of storage and without exposure to any oxidation process, we have verified that the coated microelectrodes still have the same low impedance as freshly coated microelectrodes.

In summary, the end-product delivers a high performance microelectrode and has the following qualities.

1. The coating is long lasting and it does not wear off in brain tissue.

2. The coating strongly adheres to large (i.e. macro) and small surface areas (typically less than 500 sq. microns) on at least the following metals: gold, tungsten, stainless steel, platinum, platinum-tungsten and platinum-iridium.

3. The coating has a porous structure, thereby resulting in lower impedance microelectrodes, presumably due to the greatly increased surface area provided within the z-dimension by the polymer coating. This results in a significant improvement in signal-to-noise ratio.

4. The method of coating makes it easy to coat insertion microelectrodes and MEAs.

5. This coating significantly outperforms any other coating known to the inventors.

Accordingly, in the drawings and specification, there has been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. An insertion microelectrode having an enhanced electrically effective surface providing an increased signal to noise ratio for recording purposes, said electrode comprising:
   an elongated a body having a length of at least approximately 2 millimeters and a diameter of at least approximately 40 micrometers;
   a metal surface on said body, said surface selected from gold, tungsten, stainless steel, platinum, platinum-tungsten, platinum-iridium, and combinations thereof; and
   an electrically conductive coating on said metal surface, said coating consisting essentially of a polymerized pyrrole, the polymerized pyrrole providing said microelectrode with a plurality of surface microcavities effective for promoting enhanced brain cell recordings.

2. The microelectrode of claim 1, wherein said microcavities are up to 500 nm in depth and separation.

3. The electrode of claim 1, wherein the body further includes a width and the length of the body is up to approximately 2032 millimeters and the width is up to approximately 500 micrometers.

4. The electrode of claim 1, wherein said plurality of surface microcavities comprises a depth of from approximately 2 micrometers up to about 50 micrometers.

5. An microelectrode having an enhanced electrically effective surface, said electrode comprising:
   a body;
   a metal surface on said body, said surface selected from gold, tungsten, stainless steel, platinum, platinum-tungsten, platinum-iridium, and combinations thereof; and
   an electrically conductive coating on said metal surface, said coating including polymerized pyrrole having a plurality of microcavities thereon for providing the enhanced electrically effective surface.

6. The microelectrode of claim 5, wherein the body is elongated and has length of at least approximately 2 millimeters and a diameter of at least approximately 40 micrometers.

7. The microelectrode of claim 5, wherein said microcavities of are up to 500 nm in depth and separation.

8. The electrode of claim 5, wherein the body is elongated and the length of the elongated body is up to approximately 2032 millimeters and the width is up to approximately 500 micrometers.

9. The electrode of claim 5, wherein said plurality of surface microcavities comprises a depth of from approximately 2 micrometers up to about 50 micrometers.

* * * * *